US011628091B2

(12) United States Patent
Diao et al.

(10) Patent No.: US 11,628,091 B2
(45) Date of Patent: Apr. 18, 2023

(54) MULTI-FIBER MULTI-SPOT LASER PROBE WITH SIMPLIFIED TIP CONSTRUCTION

(71) Applicant: Alcon Inc., Fribourg (CH)

(72) Inventors: Chenguang Diao, Irvine, CA (US); Mark Harrison Farley, Laguna Hills, CA (US); Alireza Mirsepassi, Irvine, CA (US); Kambiz Parto, Laguna Niguel, CA (US); Ronald T. Smith, Irvine, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/007,066

(22) Filed: Aug. 31, 2020

(65) Prior Publication Data

US 2020/0397614 A1 Dec. 24, 2020

Related U.S. Application Data

(63) Continuation of application No. 15/900,534, filed on Feb. 20, 2018, now abandoned.

(Continued)

(51) Int. Cl.
*A61B 18/22* (2006.01)
*A61F 9/008* (2006.01)
(Continued)

(52) U.S. Cl.
CPC .......... *A61F 9/00823* (2013.01); *A61B 18/22* (2013.01); *G02B 6/06* (2013.01); *G02B 6/262* (2013.01); *A61B 2018/2005* (2013.01); *A61B 2018/2025* (2013.01); *A61B 2018/2211* (2013.01); *A61B 2018/2216* (2013.01); *A61B 2018/2266* (2013.01); *A61B 2018/2272* (2013.01); *A61F 2009/00863* (2013.01)

(58) Field of Classification Search
None
See application file for complete search history.

(56) References Cited

U.S. PATENT DOCUMENTS 3,498,286 A * 3/1970 Koester .............. A61B 1/00071
600/325
4,592,353 A * 6/1986 Daikuzono ............ A61B 18/24
219/121.6

(Continued)

FOREIGN PATENT DOCUMENTS

WO 2014100075 A1 6/2014

*Primary Examiner* — Unsu Jung
*Assistant Examiner* — James Moss
(74) *Attorney, Agent, or Firm* — Patterson + Sheridan, LLP

(57) ABSTRACT

An example multi-fiber, multi-spot laser probe comprises a plurality of fibers extending from a proximal end of the laser probe to at least near a distal end of the laser probe, where the proximal end of the laser probe is configured to be coupled to a laser source via an adapter interface, and a cannula having a distal end and surrounding the plurality of fibers along at least a portion of the laser probe at or near the distal end of the laser probe, where a distal end of each of the plurality of fibers is angle-polished so that the distal end of each fiber is angled relative to a longitudinal axis of the cannula and relative to a plane perpendicular to the longitudinal axis of the cannula. Additional embodiments employ lensed fibers, a distal window, ball lens, lens array, or faceted wedge.

8 Claims, 8 Drawing Sheets

Related U.S. Application Data

(60) Provisional application No. 62/464,454, filed on Feb. 28, 2017.

(51) Int. Cl.
*G02B 6/06* (2006.01)
*G02B 6/26* (2006.01)
*A61B 18/20* (2006.01)

(56) References Cited

U.S. PATENT DOCUMENTS

| | | | | |
|---|---|---|---|---|
| 4,754,328 A | * | 6/1988 | Barath | A61B 1/042 348/359 |
| 5,703,985 A | * | 12/1997 | Owyang | A61B 18/24 385/115 |
| 5,746,738 A | * | 5/1998 | Cleary | A61B 18/24 606/15 |
| 6,096,028 A | * | 8/2000 | Bahmanyar | A61B 3/135 606/16 |
| 10,016,248 B2 | * | 7/2018 | Mirsepassi | A61B 3/1225 |
| 2002/0045811 A1 | * | 4/2002 | Kittrell | A61B 1/00096 600/407 |
| 2006/0245702 A1 | | 11/2006 | Cazzini | |
| 2007/0265602 A1 | * | 11/2007 | Mordaunt | A61F 9/008 606/4 |
| 2010/0318074 A1 | * | 12/2010 | Dacquay | A61F 9/008 606/4 |
| 2011/0144627 A1 | | 6/2011 | Smith | |
| 2013/0064515 A1 | * | 3/2013 | Shurgalin | G02B 6/3624 385/125 |
| 2013/0123760 A1 | * | 5/2013 | Spaide | A61F 9/008 606/4 |
| 2014/0121653 A1 | * | 5/2014 | Abe | A61F 9/008 606/4 |

* cited by examiner

MULTI-FIBER MULTI-SPOT LASER PROBE WITH SIMPLIFIED TIP CONSTRUCTION

PRIORITY CLAIM

This application is a continuation application of U.S. patent application Ser. No. 15/900,534 titled "MULTI-FIBER MULTI-SPOT LASER PROBE WITH SIMPLIFIED TIP CONSTRUCTION," filed on Feb. 20, 2018, whose inventors are Chenguang Diao, Mark Harrison Farley, Alireza Mirsepassi, Kambiz Parto and Ronald T. Smith, and this application further claims the benefit of priority of U.S. Provisional Patent Application Ser. No. 62/464,454 titled "MULTI-FIBER MULTI-SPOT LASER PROBE WITH SIMPLIFIED TIP CONSTRUCTION," filed on Feb. 28, 2017, whose inventors are Chenguang Diao, Mark Harrison Farley, Alireza Mirsepassi, Kambiz Parto and Ronald T. Smith (U.S. patent application Ser. No. 15/900,534 claimed the benefit of priority of U.S. Provisional Patent Application Ser. No. 62/464,454), both of which are hereby incorporated by reference in their entirety as though fully and completely set forth herein.

TECHNICAL FIELD

This application relates to a laser probe for use in ophthalmic procedures and more particularly to a multi-spot laser probe for use in photocoagulation.

BACKGROUND

Laser photocoagulation therapy addresses ocular conditions such as retinal detachments and tears as well as proliferative retinopathy resulting from diseases such as diabetes. The abnormally high blood sugar in a diabetic stimulates the retinal vessels to release growth factors that in turn encourage an undesirable proliferation of blood vessels and capillaries over the retinal surface. These proliferated blood vessels are very delicate and will readily bleed into the vitreous. The body responds to the damaged vessels by producing scar tissue, which may then cause the retina to detach so as to eventually cause blindness.

In laser photocoagulation, a laser probe is used to cauterize the blood vessels at various laser burn spots across the retina. Because the laser will also damage the rods and cones that are present in the retina to allow vision, eyesight, as well as the blood vessels, is affected. Since vision is most acute at the central macula of the retina, the surgeon arranges the resulting laser burn spots in the peripheral areas of the retina. In this fashion, some peripheral vision is sacrificed to preserve central vision. During the procedure, the surgeon drives the probe with a non-burning aiming beam such that the retinal area to be photocoagulated is illuminated. Due to the availability of low-power red laser diodes, the aiming beam is generally a low-power red laser light. Once the surgeon has positioned the laser probe so as to illuminate a desired retinal spot, the surgeon activates the laser through a foot pedal or other means to then photocoagulate the illuminated area. Having burned a retinal spot, the surgeon repositions the probe to illuminate a new spot with the aiming light, activates the laser, repositions the probe, and so on until a suitable array of burned laser spots are distributed across the retina.

The number of required laser photocoagulations for any one treatment of the retina is large. For example, 1,000 to 1,500 spots are commonly burned. It may thus be readily appreciated that if the laser probe was a multi-spot probe enabling the burning of multiple spots at a time, the photocoagulation procedure would be faster (assuming the laser source power is sufficient). Accordingly, multi-spot laser probes have been developed and can be classified into two categories. A first category, denoted herein as a "multi-fiber, multi-spot" laser probe, produces its multiple laser beams through a corresponding array of optical fibers. A second category uses only a single fiber and is thus denoted herein as a "single-fiber, multi-spot" laser probe. Regardless of whether a laser probe is a single-fiber or multi-fiber probe, it should be compatible with the adapter used to connect the probes to the laser source. In that regard, it is conventional for a laser source to have a standardized interconnect such as a subminiature version A (SMA) interconnect. For example, the laser source may have a female SMA connector that receives a male SMA connector coupled to whatever instrument the laser source is driving. For a conventional single-fiber, single-spot laser probe, its male SMA connector will incorporate a single fiber. The laser source provides a focused beam known as the laser beam waist to the male SMA connector. This is quite advantageous for the single fiber probe since its optical fiber has its end face illuminated by the waist to enable efficient coupling to the laser source. But if a multi-fiber, multi-spot laser probe uses a corresponding plurality of fibers to drive its multiple spots, it cannot simply have its multiple fibers receive the focused beam from the source in this convenient single-fiber fashion because the laser waist is too narrow to couple into multiple fibers. Instead, the laser source would have to have its conventional interconnect changed or adapted so that the multiple fibers from the probe are not simply presented with the laser waist. But such changes are expensive and cumbersome.

Thus, a multi-fiber, multi-spot probe has been developed such that the laser source drives a single fiber interconnect connected to a single fiber cable that in turn drives a single-fiber/multiple-fiber optical coupling within the laser probe handpiece. The resulting optics within the handpiece increase costs because it is desirable that the laser probe be disposable to limit contamination from patient to patient. For example, the optics include a diffractive beam splitter to split the beam from the single fiber into multiple beams for distribution to the multiple fibers. To collimate the laser beam from the single fiber onto the beam splitter and then condense the resulting multiple beams onto the multiple fibers requires plano-convex lenses. But it is very difficult to move such lenses to the laser source interconnect such that the remainder of the probe can be less expensive because of the relatively small inner diameter of such interconnects.

Another issue arises in multi-fiber, multi-spot laser probes in that the telecentric laser beams transmitted from the distal ends of the multiple fibers should be directed into different angular directions so as to properly distribute the resulting laser beam spots on the retina. To provide such distribution, a multi-fiber, multi-spot laser probe has been developed with the distal ends of the fibers bent into the desired angular directions. But such bending is cumbersome and increases costs as well.

To avoid the issues associated with the use of multiple fibers, the light beam from a single-fiber laser probe can be directed onto a diffractive beam splitter that splits the beam into multiple diffracted beams for transmission to the retina. However, the diffractive beam splitter must then focus the resulting diffracted beams, which requires the grating prescription to be spatially varying across the element. Not only does such a complication increase costs, the resulting spatially-varying diffractive beam splitter will reduce the overall performance. Such a design also makes varying the distance between the distal fiber end the diffractive element difficult.

Accordingly, there is a need in the art for improved multi-spot laser probes.

SUMMARY

Embodiments disclosed herein eliminate the need for a gradient-index (GRIN) lens at the distal end of a multi-fiber multi-spot laser probe by means of direct beam output from cleaved, polished, or lensed fibers. Additional embodiments employ a distal window, ball lens, lens array, or faceted wedge.

An example multi-fiber, multi-spot, laser probe according to some embodiments disclosed herein comprises a plurality of fibers extending from a proximal end of the laser probe to at least near a distal end of the laser probe, where the proximal end of the laser probe is configured to be coupled to a laser source via an adapter interface, and a cannula having a distal end and surrounding the plurality of fibers along at least a portion of the laser probe at or near the distal end of the laser probe, where a distal end of each of the plurality of fibers is angle-polished so that the distal end is angled relative to a longitudinal axis of the cannula and relative to every perpendicular to the longitudinal axis of the cannula.

Another example of a multi-fiber, multi-spot laser probe according to some of the embodiments disclosed herein comprises a plurality of fibers extending from a proximal end of the laser probe to at least near a distal end of the laser probe, where the proximal end of the laser probe is configured to be coupled to a laser source via an adapter interface, and a cannula having a distal end and surrounding the plurality of fibers along at least a portion of the laser probe at or near the distal end of the laser probe. These embodiments further comprise a spacer arranged within the cannula along a portion of the laser probe at or near the distal end of the laser probe, the spacer being configured to guide at least one of the plurality of the fibers so that a distal portion of each of at least one of the plurality of fibers is oriented at an angle, relative to a longitudinal axis of the cannula.

In some of these latter embodiments, the spacer is a helical spacer, the helical spacer being configured so that the plurality of fibers are arranged in a helical configuration, near the distal end of the laser probe. In others, the spacer is configured to force a distal portion of each of the plurality fibers in an angular direction away from the longitudinal axis of the cannula. In still others, the spacer is configured to force a distal portion of each of the plurality fibers in an angular direction towards the longitudinal axis of the cannula. In yet others, the spacer is configured to bend a distal portion of each of one or more of the plurality of fibers angularly, in corresponding offset planes relative to orthogonal central planes intersecting the longitudinal axis of the cannula, so that beams emitted from the distal ends of the fibers diverge.

Another example of a multi-fiber, multi-spot laser probe according to some of the embodiments disclosed herein comprises a plurality of fibers extending from a proximal end of the laser probe to at least near a distal end of the laser probe, again where the proximal end of the laser probe is configured to be coupled to a laser source via an adapter interface, and a cannula having a distal end and surrounding the plurality of fibers along at least a portion of the laser probe at or near the distal end of the laser probe. These embodiments further comprise a lens mechanism arranged within the cannula at or near the distal end of the laser probe, the lens mechanism being arranged so that beams emitted from the distal ends of the fibers pass through the lens mechanism. The lens mechanism in these embodiments does not comprise a gradient-index (GRIN) lens.

In some of these embodiments, the lens mechanism comprises a lensed distal end arranged on each of the plurality of fibers. In others, the lens mechanism comprises a micro-lens array having a plurality of lens elements disposed adjacent to corresponding distal ends of the plurality of fibers. In still others, the lens mechanism comprises a single ball lens disposed adjacent to distal ends of the plurality of fibers, so that beams emitted by the plurality of fibers pass through the single ball lens. In still others, the lens mechanism comprises a plano-convex lens disposed adjacent to distal ends of the plurality of fibers, where the distal end of each of the plurality of fibers is angle-polished so that the distal end is angled relative to a radial axis of the cannula and relative to every perpendicular to the radial axis of the cannula, with the angled-polished distal ends of the fibers being oriented such that the distal ends of the plurality of fibers emit corresponding beams that converge towards the radial axis of the cannula. In some embodiments, the lens mechanism is replaced with a micro-wedge array having a plurality of wedge elements disposed adjacent to corresponding distal ends of the plurality of fibers.

BRIEF DESCRIPTION OF THE FIGURES

FIG. 6B illustrates an example embodiment of a distal end of a multi-fiber, multi-spot laser probe that incorporates angle-polished distal fiber faces and a window element.

DETAILED DESCRIPTION

Described in detail herein are improved multi-fiber, multi-spot laser probes that are compatible with conventional laser source interconnects.

Figure 1:
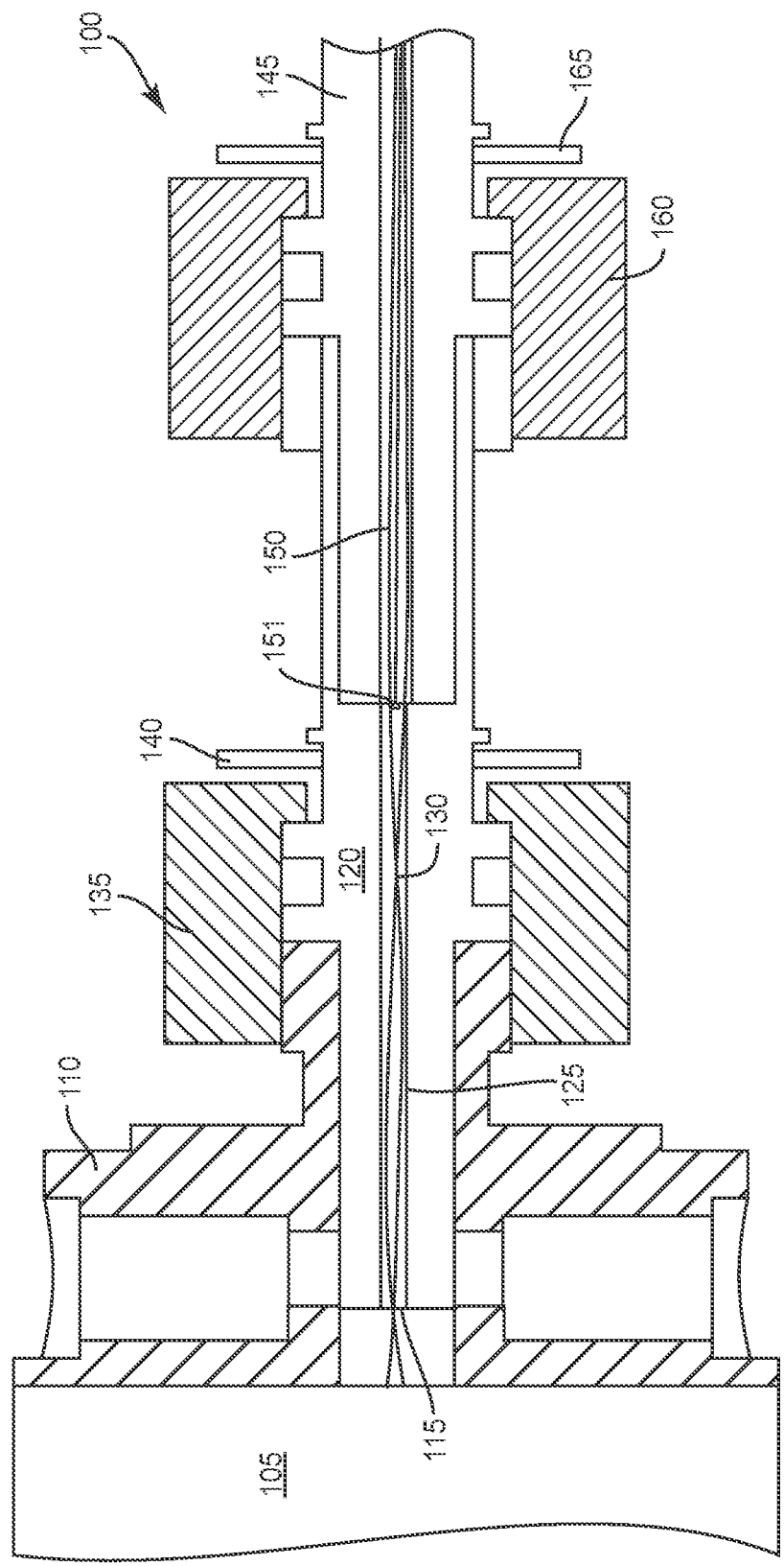
FIG. 1 is a longitudinal cross-sectional view of a laser source coupled to an adapter element containing a gradient-index (GRIN) lens for coupling to a proximal end of a multi-fiber, multi-spot laser probe.

Turning now to the drawings, certain details of a multi-fiber, multi-spot laser probe 100 are shown in FIG. 1. Not shown in FIG. 1 are details of the proximal end of laser probe 100; details of several realizations of the proximal end are provided below. The portions of the multi-fiber, multi-spot laser probe 100 shown in FIG. 1 are also illustrated in U.S. Pat. No. 8,951,244; thus, it will be appreciated that the details shown in FIG. 1 represent an example of the prior art.

Returning to FIG. 1, it can be seen that a laser source 105 drives probe 100 through a suitable interconnect. A common standardized interconnect for laser source 105 is a subminiature version A (SMA) adapter. Thus, laser source 105 includes a female SMA adapter 110. However, it will be appreciated that laser probe 100 is readily adapted to mate with any conventional standardized optical interconnect so long as the laser source's interconnect presents a focused beam spot such as laser waist 115 to a proximal end of a male connector from the laser probe. Thus, the following discussion will assume that laser probe 100 couples to source 105 through a customized SMA adapter 120 without loss of generality.

To receive laser waist 115, the bore of SMA adapter 120 includes a gradient index (GRIN) lens 125. GRIN lens 125 may be a simple, single-element cylindrical GRIN rod lens that is readily inserted into such a bore. GRIN lens 125 is designed to relay the focused beam to a second focused spot 130 and then to a collimated beam wave front at its distal end. As known in the SMA arts, SMA adapter 120 secures to SMA adapter 110 through a threaded cylinder 135 and retaining ring 140. SMA adapter 120 has both a male end for insertion into SMA adapter 110 but also a female end that receives a conventional optical interconnect such a male SMA 905 fiber connector 145. Connecter 145 secures to adapter 120 through a threaded cylinder or ring 160 and retaining ring 165. Connector 145 includes in its bore an array of optical fibers 150. A proximal end 151 of array 150 is separated from the distal end of GRIN lens 125 by a suitable air gap such as a 220 µm air gap. Connector 145 connects to a flexible cable encasing fibers 150 that leads to a handpiece and cannula, as known in the laser probe arts.

Figure 2:
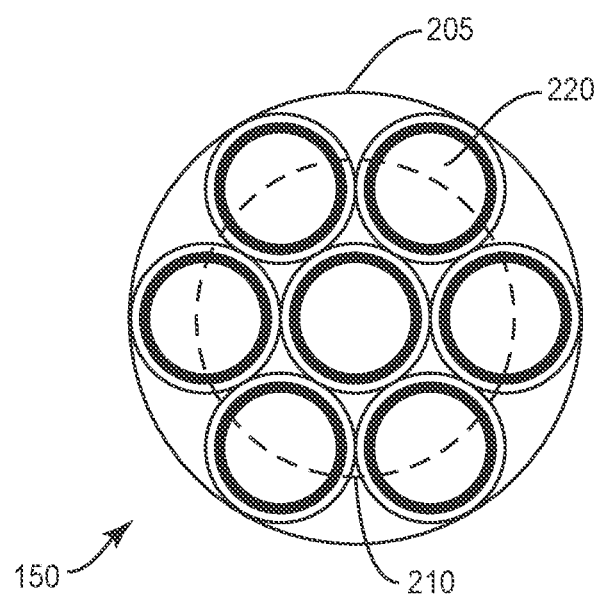
FIG. 2 shows a radial cross-sectional view of a multi-fiber array within the proximal end of the probe of FIG. 1.

An example embodiment of fiber array 150 is shown in cross-section in FIG. 2. The laser beam boundary at the proximal end 151 of FIG. 1 is shown for both a green laser beam boundary 205 from source 105 as well as a red aiming beam boundary 210. Array 150 includes a central fiber circumferentially surrounded by six outer fibers. In one embodiment, each fiber 220 has a numerical aperture (NA) of 0.22 achieved through a 75 µm glass core encased in a 90 µm cladding, surrounded by a 101 µm jacket. To minimize the amount of uncoupled laser energy into array 150, GRIN lens 125 is configured such that laser beam boundary 205 just encompasses the six outer fibers. The clocking of array 150 relative to the laser beam is not an issue as the laser beam and array 150 are at least generally axisymmetric. Array 150 extends to a distal end of the laser probe; details of several embodiments of the distal end of the laser probe are discussed in more detail below.

The advantageous properties of such a proximal interconnection in that no complicated, multi-lens relay system is required. Instead, GRIN lens 125 is readily inserted into the bore of adapter 120 that enables a standardized adapter such as male SMA adapter 145 to attach a disposable laser probe receiving fiber array 150. Without GRIN lens 125 and its adapter 120, standardized adapter 110 on laser source 105 would have to be changed, which is plainly undesirable since other attachments for source 105 would have to change in concert. Alternatively, the source's adapter could be left standardized but then a multi-lens relay system would be required. However, SMA adapter 120 and GRIN lens 125 eliminate such complications. Although SMA adapter 120 is thus quite advantageous, one can appreciate that roughly 50% of the laser energy is delivered to the interstices between the fibers in array 150 as seen in FIG. 2. This laser energy is thus unavailable for use in photocoagulation, thereby increasing the necessary laser source power and/or the amount of time necessary to produce the laser burn spots.

Figure 3:
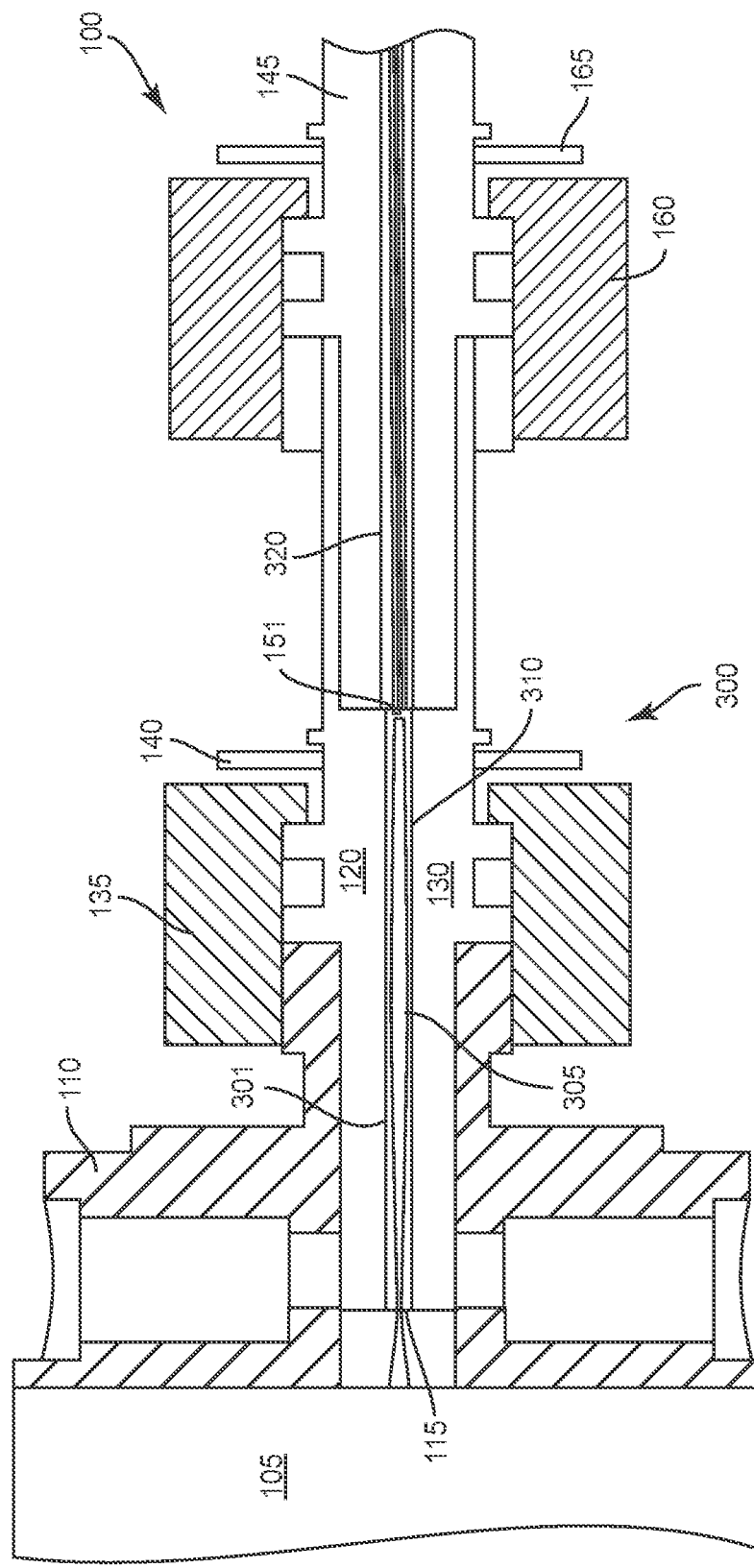
FIG. 3 is a longitudinal cross-sectional view of a laser source coupled to an adapter element including a diffractive beam splitter for coupling to a proximal end of a multi-fiber, multi-spot laser probe.
Figure 4:
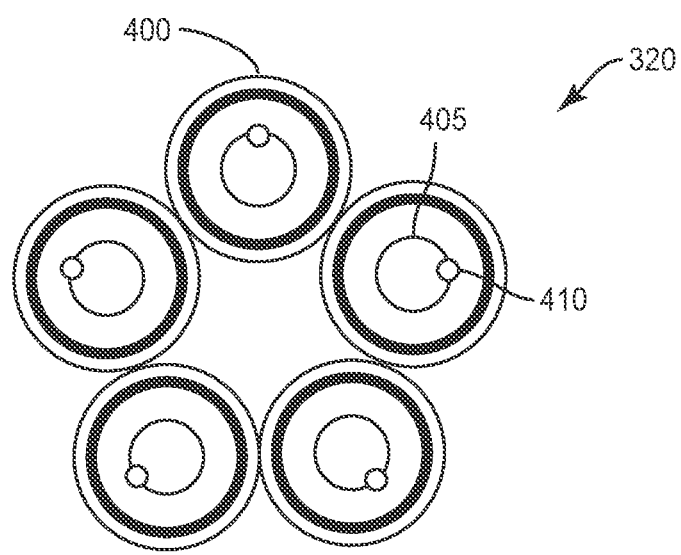
FIG. 4 is a radial cross-sectional view of a multi-fiber array within the proximal end of the probe of FIG. 3.

Turning now to FIG. 3, a diffractive embodiment that does not illuminate fiber array interstices is illustrated. As discussed with regard to FIG. 1, customized SMA adapter 120 permits a user to conveniently attach a disposable probe to adapter 120 to drive laser energy onto a fiber array. In the embodiment shown in FIG. 1, however, adapter 120 includes in its bore a diffractive beam splitter 305 arranged between a first GRIN lens 301 and a second GRIN lens 310. GRIN lens 301 is configured to collimate the laser beam diverging from laser waist 115 into a collimated wave front presented to diffractive beam splitter 305. GRIN lens 310 is configured to focus the resulting diffracted multiple laser beams from splitter 305 onto a proximal face 151 of a fiber array 320 contained within the bore of male SMA adapter 145. Fiber array 320 includes a plurality of fibers arranged according to the diffractive properties of diffractive beam splitter 305. For example, if diffractive beam splitter produces a symmetric pentagonal distribution of five diffracted beams, fiber array 320 is arranged in a corresponding pentagonal distribution. FIG. 4 shows such an arrangement for fiber bundle 320 at its proximal face 151.

In one embodiment, each optical fiber 400 has a 75 µm glass core clad in a 90 µm cladding, which in turn is surrounded by a 101 µm jacket, to achieve an NA of 0.22. The resulting projection of the diffracted green laser beams from splitter 305 is indicated by a boundary 405. Because diffraction is wavelength dependent, the projection of the aiming beam will have a different alignment with fiber array 320. Thus, splitter 305 and fiber array 320 are arranged such that boundary 405 is axially aligned with each fiber 400, whereas a boundary 410 of a red aiming beam is radially displaced with regard to a center or longitudinal axis of each fiber.

In one embodiment, the off-axis displacement provided by splitter 305 to each green diffracted beam is 1.45 degrees. GRIN lens 310 focuses the resulting collimated and diffracted beams onto the entrance face of each fiber 400 in array 320. By such an appropriate clocking of array 320 relative to the diffracted beams, efficient coupling of the respective diffracted beam and the aiming beam into each fiber 400 is achieved. In that regard, other types of adapters such as a ferrule connector (FC) or a standard connector (SC) commonly used in the telecommunications industry may be used instead of SMA adapter 120 to assist in optimal clocking. As discussed with regard to FIG. 1, assembly of the optical components into SMA adapter 120 is advantageously convenient in that GRIN lenses 301 and 310 as well as intervening diffractive beam splitter 305 may have optical adhesive applied and then slid into the bore of adapter 120 and abutted end-to-end with each other. In contrast, an alignment of refractive lenses would be cumbersome and difficult in comparison.

Figure 5:
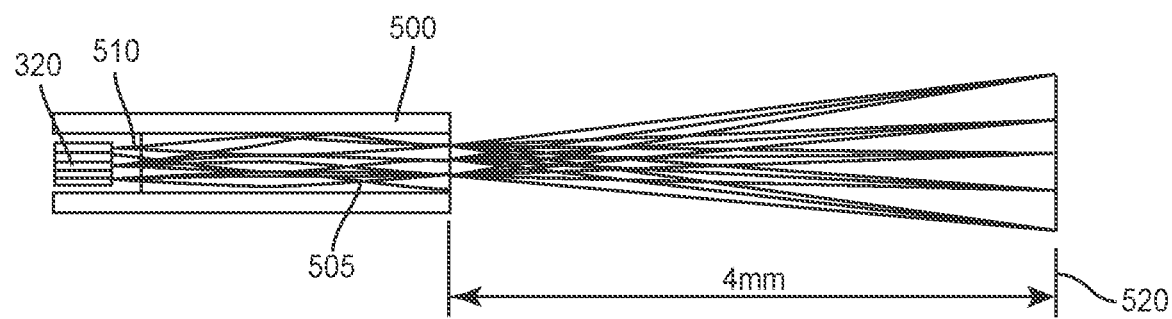
FIG. 5 illustrates a GRIN lens for angularly separating the projected multiple beams emitted from the multi-fiber array of FIG. 4.

With the laser beam from the source split and telecentrically propagated through the fiber array as discussed above with regard to either FIG. 1 or FIG. 3, there remains the issue of angularly projecting focused laser spots from the laser probe. U.S. Pat. No. 8,951,244 disclosed a GRIN lens solution, an example of which is shown in FIG. 5. It will be appreciated that while the example embodiment shown in FIG. 5 is particularly adapted for compatibility with the fiber array 320 of FIG. 3, it will be appreciated that an analogous embodiment can be readily constructed for fiber array 150 of FIG. 1.

As seen in FIG. 5, a laser probe cannula 500, e.g., a stainless steel cannula, receives a GRIN lens 505 at its distal end. A distal end of fiber array 320 is displaced within the cannula so as to project diverging beams 510 at a proximal end face of GRIN lens 505. GRIN lens 505 then focuses the beams on the retinal surface 520. The distribution of the resulting focused beams on the retina depends on the distribution of the fibers at the distal end of array 320.

In that regard, whereas the distribution at the proximal end of array 320 (FIG. 3) should be axially symmetric, one can arrange the fibers in any suitable distribution at the distal end. For example, as seen in FIG. 5, array 320 is linearly arranged at the distal end. The resulting laser spots are thus an enlarged version of the image (in this embodiment, a linear array) presented to GRIN lens 505. In one embodiment, GRIN lens 505 focuses the angularly-distributed beams at a distance of 4 mm from the distal end of cannula 500. Advantageously, GRIN lens 505 obviates any need for: bending the fibers into the desired angular distribution (and the associated problems of such bending), beveling the distal end faces of the fibers, or adding optical elements to the distal end faces. The fibers can even be touching one another in array 320 and GRIN lens 505 will still be effective.

In the following, several alternatives to the configuration shown in FIG. 5 for the distal end of a multi-fiber multi-spot laser probe are described in detail. These embodiments have in common that the GRIN lens 505 is removed from the laser beam path at the probe's distal end. Test data have shown certain GRIN lens materials to be susceptible to decreased thermal reliability due to absorption of optical power in certain environments and operating conditions. This increased absorption is associated with certain GRIN lens materials, and may thus be alleviated by embodiments that eliminate the use of optics distal to the laser transmission optical fibers, or that use distal optics made from non-GRIN materials, such as pure fused silica or other standard optical glasses having low optical absorption. It will be appreciated, then, that the several embodiments detailed herein may improve thermal reliability, while providing optical performance similar to the device shown in FIG. 5.

As will be discussed in greater detail below, several of the embodiments disclosed herein eliminate the need for a GRIN lens at the distal end of the multi-fiber multi-spot laser probe by means of direct beam output from cleaved, polished, or lensed fibers. Additional embodiments employ a distal window, ball lens, lens array, or faceted wedge.

The several embodiments detailed below are presented with respect to 4-fiber or 5-fiber embodiments of the invention, which are shown in axial and transverse cross section views. It will be understood, however, that the number of fibers is not limited to 4 or 5. Further, the embodiments are not presented in any particular order. The embodiments disclosed herein may be implemented in laser probes that are compatible with either of the adapters described above, i.e., in FIGS. 1 and 3, which provide means for splitting the beam and focusing the resulting multiple beams into the proximal ends of optical fibers, such that each fiber carries its own beam. It will be understood, however, that the embodiments described below may be implemented in laser probes having different mating configurations at the proximal end, and/or in conjunction with different adapters or interfaces for coupling a laser source or sources to the multiple fibers of the multi-fiber laser probe.

Figure 6A:
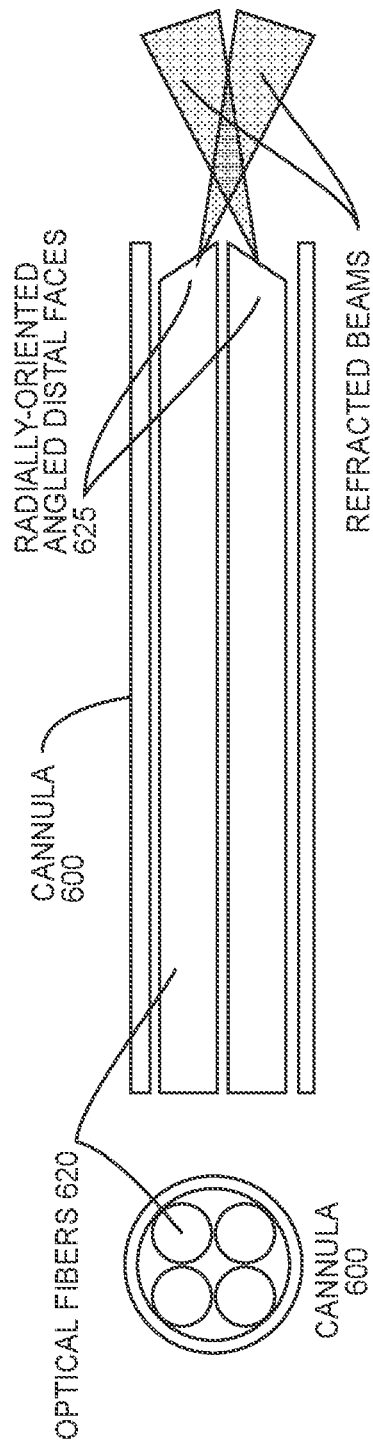
FIGS. 6A and 6B illustrates an example embodiment of a distal end of a multi-fiber, multi-spot laser probe that incorporates angle-polished distal fiber faces.

A first example embodiment of the distal end of a multi-fiber multi-spot laser probe that omits a GRIN lens at the distal end is shown in FIG. 6A. This embodiment utilizes angle-polished distal fiber faces. More particularly, the embodiment shown in FIG. 6A comprises straight fibers 620, with each fiber 620 having an end 625 polished at an angle. The fibers 620 are oriented so that the radially-oriented angled distal faces refract light substantially inwards, radially, such that the beams converge, beyond the end of cannula 600, at the center, longitudinal, axis of the cannula 600, before diverging and separating with increasing working distance.

Figure 6B:
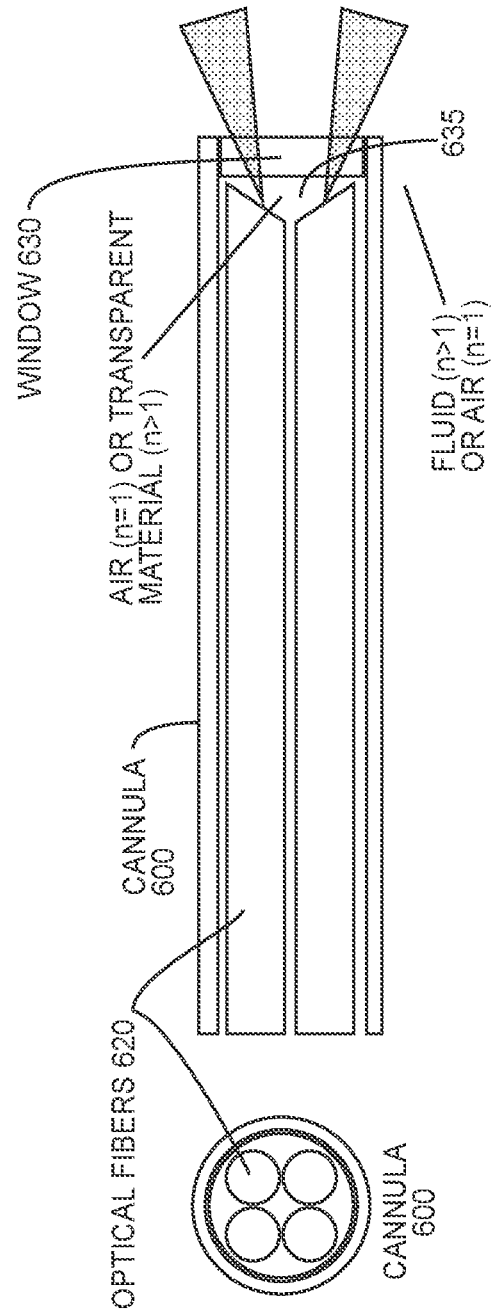

Alternatively, the fibers 620 may be axially rotated so as to refract light substantially outward, as shown in the alternative embodiment of FIG. 6B, such that the beams form a diverging spot pattern increasing in size and separation distance with increasing working distance from the distal end of cannula 600.

The converging-beam arrangement shown in FIG. 6A has some advantages over the diverging-beam arrangement, including as that the fibers 620 can be recessed well into the cannula 600 for increased protection, without the cannula walls shadowing the emerging beams. Further, the point at which the beams converge, at a short working distance from the tip, can be used by surgeons to create a single treatment spot for certain procedures such as repair of retinal breaks and tears. On the other hand, the diverging-beam arrangement, as exemplified by FIG. 6B, has certain advantages over the converging-beam arrangement, including that the working distance that achieves a pattern of spots with a given separation distance is shorter, for the diverging-beam arrangement.

It will be noted that the embodiment shown in FIG. 6B includes a window 630 situated in front of the angle polished fibers, to form an internal chamber 635 that can be filled with air or a transparent material such as a fluid, gel, adhesive or sealant. The window 630, which need not appear in all embodiments of the diverging-beam configuration of the distal probe end described herein, can decrease sensitivity of the beam divergence to optical media through which the beams propagate distally from the probe. The probe can thus perform similarly for example in air (n=1), BSS (n=1.36), and other fluids used in ophthalmic surgery, a plurality of which may sometimes be present in the same surgical case.

Figure 7:
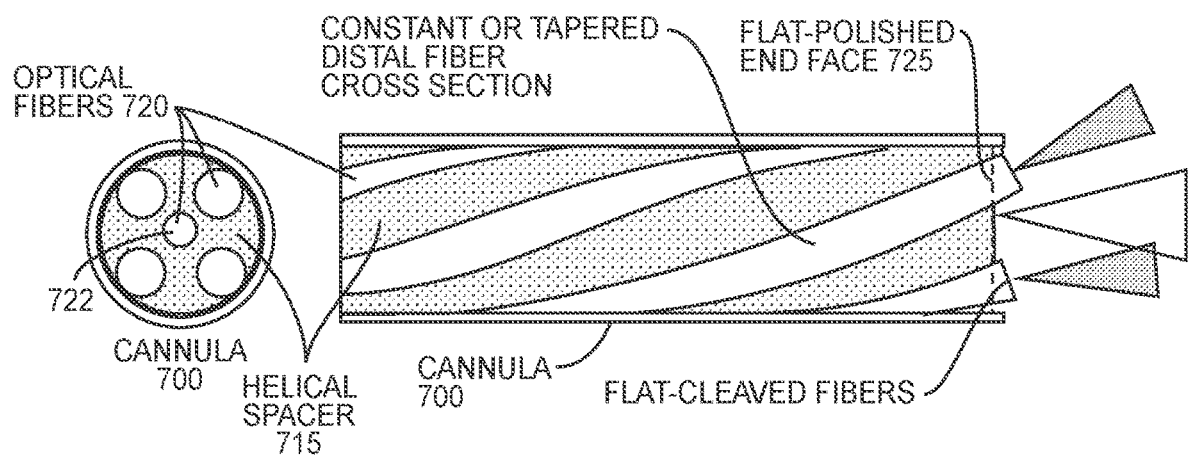
FIG. 7 illustrates an example embodiment of a distal end of a multi-fiber, multi-spot laser probe that incorporates fibers arranged around a helical spacer.

FIG. 7 illustrates another example embodiment of the distal end of a multi-fiber multi-spot laser probe, where the laser probe in this case includes fibers 720 situated around a helical spacer 715, arranged within cannula 700. As seen in FIG. 7, the fiber ends 725 are flat-polished or flat-cleaved. The distal fiber cross section may be constant, or tapered in order to provide the desired divergence of each beam. The embodiment shown in FIG. 7 creates tangential angular separation of the fibers by arranging them in a helical configuration. This has several advantages, including that the required diametrical space is less than that required for radial angular separation of fibers, thereby allowing a smaller gauge size for cannula 700. Further, the fibers 720 can be flat cleaved or flat-polished to a common planar exit surface with the other fibers, resulting in an end face angle of only a few degrees, creating a more compact, less elliptical output beam shape than the angle-polished designs in FIGS. 6A and 6B. Still further, the central area between fibers is continuous, and thus available for an additional, but optional, fiber 722 routed along the center. This center fiber 722 can be used to deliver a separate, single beam of the same type or a different wavelength, for example, broadband illumination, simultaneously or independently of the other beams.

As noted above, the embodiment shown in FIG. 7 includes a space where an additional fiber or fibers may be routed along a central portion of cannula 700. It will be appreciated that several other embodiments described herein may provide routes along the cannula for an additional fiber or fibers. In any of these embodiments, an additional fiber may be the same or a similar type as the other fibers, but may be routed to a separate source at the input end, so as to deliver the same wavelength and beam characteristics as the other fibers, but in a single beam used simultaneously or alternately. This single-beam delivery capability can provide complementary functionality in complex surgeries, and may address a greater variety of uses, for example where multi-spot delivery is advantageous for procedures such as pan-retinal photocoagulation (PRP), but where single-spot delivery is advantageous, such as for procedures to repair retinal breaks and tears. An additional fiber may also be of a different type suitable for delivery of different wavelengths and beam characteristics, such as broad-spectrum, wide-angle illumination, or suitable for receiving light for sensing purposes sensing, such as in a reflective proximity sensor.

The example embodiment shown in FIG. 7, as well as most others disclosed herein, may incorporate tapered distal cross section profiles of the fibers to modify the output beam characteristics. For example, the distal fibers may be tapered to a larger cross section near the distal end, to reduce the divergence of each beam. Conversely, the fibers may be tapered to a smaller cross section, to increase their respective beam divergences.

Figure 8:
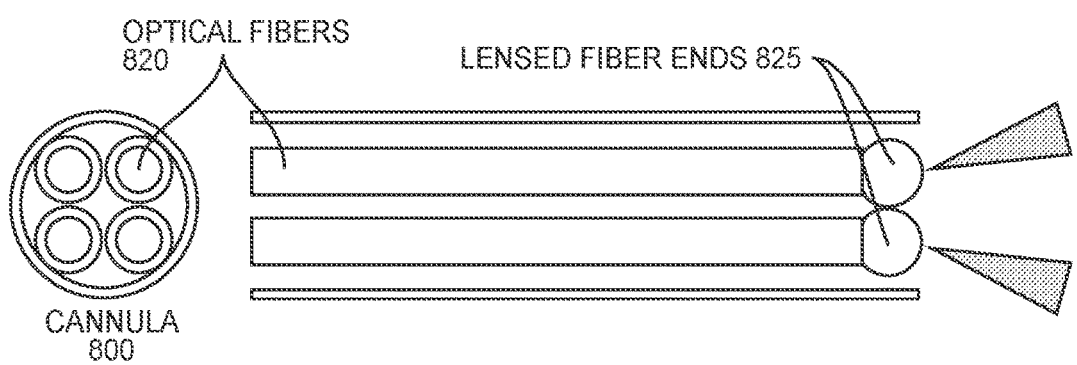
FIG. 8 illustrates an example embodiment of a distal end of a multi-fiber, multi-spot laser probe that incorporates lensed fiber ends.

FIG. 8 illustrates an example implementation of the distal end of a multi-fiber, multi-spot laser probe in which lensing of the distal fiber ends is incorporated. The lenses 825 at the distal ends of fibers 820 may be configured, in various embodiments, to provide beams with near-field focus, collimation, or mildly diverging properties. These can provide several advantages, depending on the degree of beam focusing, including that stronger beam focusing can provide near-field convergence of the individual beams that can substantially overlap, providing essentially a single beam at a working distance approximately equal to the focal length, while providing individual beams at longer working distances. Alternatively, lenses adapted to provide collimation or near-collimation can provide a design that is insensitive to working distance and therefore provides greater ease of use, with smaller spots, and thus requires less total power to provide the required intensity for surgical treatment. Lenses configured to provide slight beam divergence can be used to provide embodiments that produce adequate spot separation at shorter working distances, while still providing relatively low sensitivity to working distance, compared to the raw output from non-lensed fibers.

Figure 9:
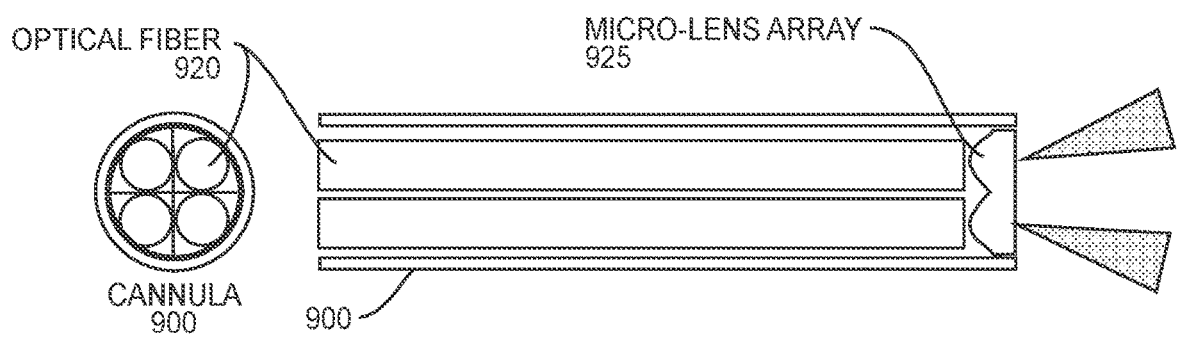
FIG. 9 illustrates an embodiment that incorporates a micro-lens array at the distal end of the multi-fiber multi-spot laser probe.
Figure 10:
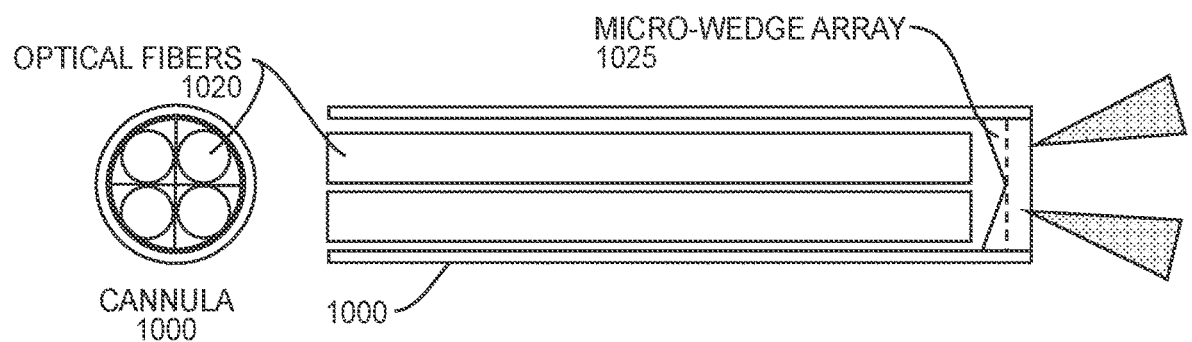
FIG. 10 illustrates an embodiment that incorporates a micro-wedge array at the distal end of the multi-fiber multi-spot laser probe.

The embodiments shown in FIGS. 9 and 10 provide advantages like those of the lensed-fiber embodiments exemplified by FIG. 8, but use a single array of lens or wedge elements, with each element of the array being paired with a corresponding fiber. Additionally, this approach enables the use of aspherical lens surfaces to further tune beam divergence, spot spacing and spot shape. The embodiment shown in FIG. 9 incorporates a micro-lens array 925, while the embodiment of FIG. 10 includes a micro-wedge array 1025.

Figure 11:
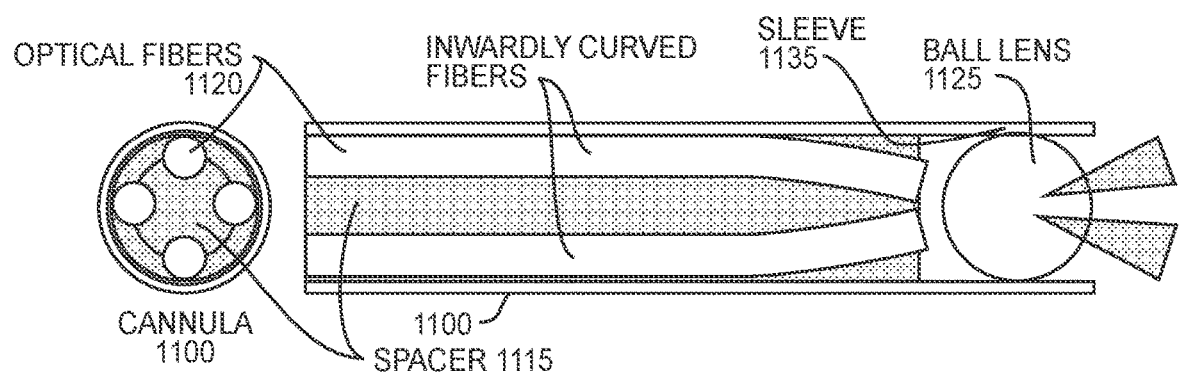
FIG. 11 illustrates an embodiment that incorporates a single ball lens at the distal end of the laser probe.

FIG. 11 illustrates an embodiment that incorporates a single ball lens 1125, coupled with the use of inwardly curved fibers 1120, which are guided inward with a spacer 1115. This embodiment provides similar advantages to those provided by the embodiments of FIGS. 8-10, but with the use of a single spherical lens through which all of the beams travel. Each fiber is angled to project its corresponding beam towards the center of the ball lens. This minimizes the amount of spherical aberration from the ball lens and results in tightly focused spots at the retinal plane with maximum separation between adjacent spot edges and minimum light spilling over between adjacent spots.

Figure 12:
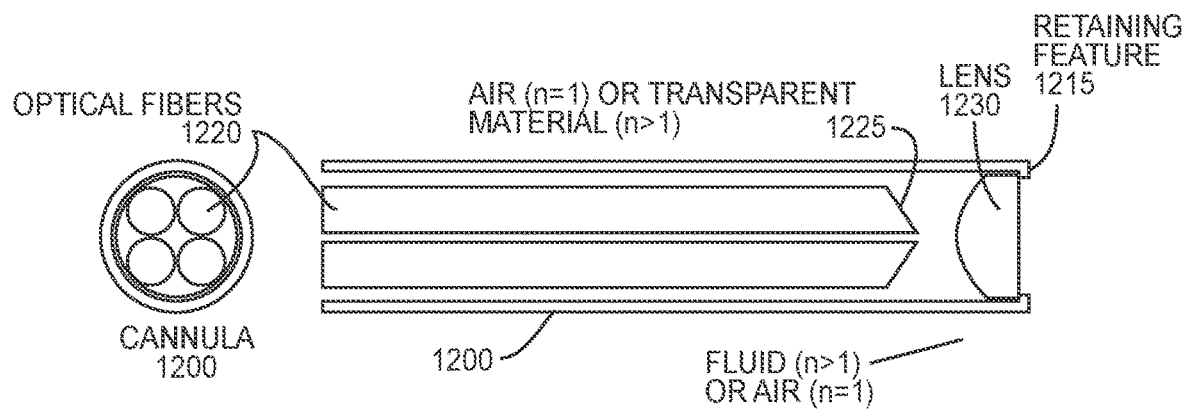
FIG. 12 illustrates an embodiment that incorporates angle-polished distal fiber faces as well as a plano-convex lens and retaining feature.

FIG. 12 illustrates an example embodiment that incorporates both angle-polished distal fiber faces 1225 and a plano-convex lens 1230. In the example embodiment shown in FIG. 12, plano-convex lens 1230 is held within cannula 1200 with a retaining feature 1215. It will be appreciated that the embodiment shown in FIG. 12 combines the advantages of several of the embodiments described above, e.g., as illustrated in FIGS. 6A, 6B, and 8-11. The wedges are used to angle the beams towards the center of the plano-convex lens, for the same reasons that were described in the previous paragraph.

Figure 13:
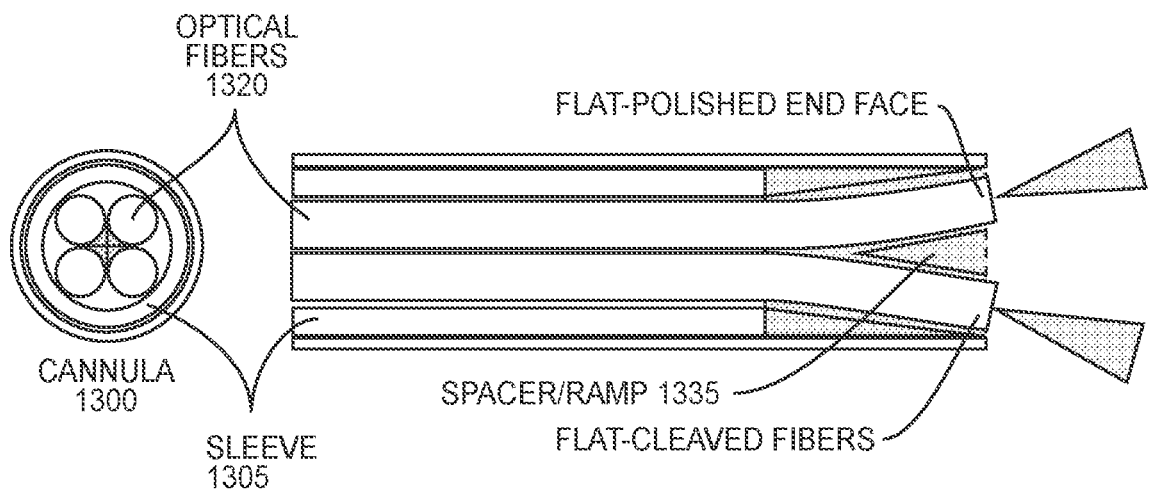
FIG. 13 illustrates an embodiment that arranges fibers on a radial ramp.

FIG. 13 illustrates an example embodiment that achieves spot separation by bending of the fibers angularly in essentially a radial direction outward, to produce a diverging beam pattern. This is achieved with the use of a spacer in the form of a radial ramp 1335, situated between the fibers 1320. A sleeve 1305, between the cannula 1300 and the fibers 1320, keeps the fibers 1320 arranged against the ramp 1315. Alternatively, an internal spacer 1115 and a sleeve 1135 can be arranged to force the fibers 1120 radially inward, i.e., as shown in FIG. 11, but without the ball lens, to produce a converging beam pattern. These embodiments provide the advantage of simple construction and high reliability. The converging beam pattern has the additional advantage of producing a single spot at a near working distance, and a pattern of separate spots at a farther working distance.

Figure 14:
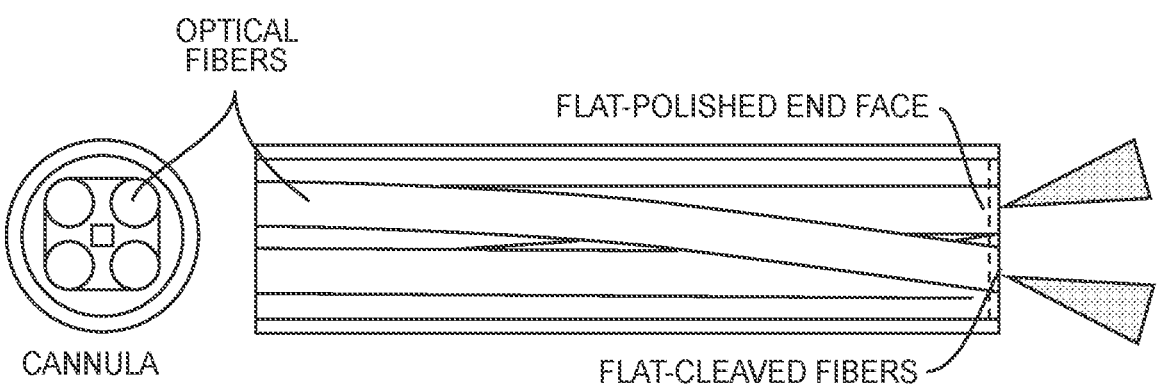
FIG. 14 illustrates an embodiment that incorporates fibers arranged with a planar-offset bypass.

FIG. 14 illustrates still another embodiment, this one incorporating fibers with planar-offset bypass. This embodiment achieves spot separation by bending of the fibers angularly in offset planes relative to the orthogonal central planes intersecting the cannula axis, as shown in the figure, to produce a diverging beam pattern.

Embodiments described above illustrate but do not limit the invention. It should also be understood that numerous modifications and variations are possible in accordance with the principles of the present invention. Accordingly, the scope of the invention is defined only by the following claims.

What is claimed is:
1. A multi-fiber, multi-spot laser probe, comprising:
a plurality of fibers extending from a proximal end of the laser probe to at least near a distal end of the laser probe, wherein the proximal end of the laser probe is configured to be coupled to a laser source;
a cannula having a distal end and surrounding the plurality of fibers along at least a portion of the laser probe at or near the distal end of the laser probe; and
a spacer arranged within the cannula along a portion of the laser probe at or near the distal end of the laser probe, the spacer being configured to guide at least one of the plurality of the fibers so that a distal portion of each of the at least one of the plurality of fibers is oriented at an angle, relative to a longitudinal axis of the cannula;

wherein the spacer comprises a longitudinal channel disposed generally along a central longitudinal axis of the spacer and extending to at or near the distal end of the laser probe, and wherein the multi-fiber, multi-spot, laser probe further comprises a longitudinal fiber arranged in the longitudinal channel and extending to at or near the distal end of the laser probe;

wherein the longitudinal fiber has a different diameter than each of the plurality of fibers;

wherein the plurality of fibers do not include the longitudinal fiber;

wherein the spacer is a helical spacer, the helical spacer being configured so that each of the at least one of the plurality of fibers is arranged in a helical configuration, near the distal end of the laser probe; and wherein the spacer is configured to bend the distal portion of each of the at least one of the plurality of fibers so that the distal portion of each of the at least one of the plurality of fibers in the helical configuration is tangentially angularly separated from a distal portion of another one of the plurality of fibers and each of the at least one of the plurality of fibers emits a beam in a different direction diverging from the longitudinal axis.

2. The multi-fiber, multi-spot laser probe of claim 1, wherein the distal end of each of the plurality of fibers is angle-polished so that a distal end face of each fiber of the plurality of fibers is angled relative to a longitudinal axis of the cannula and relative to a plane perpendicular to the longitudinal axis of the cannula.

3. The multi-fiber, multi-spot laser probe of claim 2, wherein the angled-polished distal ends of the fibers of the plurality of fibers are oriented such that the distal portions of the plurality of fibers emit corresponding beams that diverge away from the longitudinal axis of the cannula.

4. The multi-fiber, multi-spot laser probe of claim 3, further comprising:
   a window element situated at or near the distal end of the cannula and arranged so that the corresponding beams pass through the window element; and
   a fluid, gel, adhesive, or sealant disposed inside the cannula, between the window element and the distal ends of the plurality of fibers.

5. The multi-fiber, multi-spot laser probe of claim 1, wherein the spacer is configured to force the distal portion of each of the plurality of fibers in an angular direction away from the longitudinal axis of the cannula.

6. The multi-fiber, multi-spot laser probe of claim 1, wherein each of the plurality of fibers has a tapered cross-section, near the distal portion of the fibers of the plurality of fibers.

7. The multi-fiber, multi-spot laser probe of claim 6, wherein each fiber of the plurality of fibers is tapered so as to have a larger cross-section near the distal end, relative to its cross-section further towards the proximal end of the laser probe.

8. The multi-fiber, multi-spot laser probe of claim 6, wherein each fiber of the plurality of fibers is tapered so as to have a smaller cross-section near the distal end, relative to its cross-section further towards the proximal end of the laser probe.

* * * * *